United States Patent [19]

Brinkwerth et al.

[11] Patent Number: 4,610,807
[45] Date of Patent: Sep. 9, 1986

[54] DISTYRYL COMPOUNDS

[75] Inventors: Wolfgang Brinkwerth, Leverkusen; Udo Eckstein, Cologne, both of Fed. Rep. of Germany

[73] Assignee: Bayer Aktiengesellschaft, Leverkusen, Fed. Rep. of Germany

[21] Appl. No.: 662,470

[22] Filed: Oct. 18, 1984

[30] Foreign Application Priority Data

Oct. 29, 1983 [DE] Fed. Rep. of Germany ....... 3339383

[51] Int. Cl.⁴ ............................................. C09K 11/06
[52] U.S. Cl. .................................. 252/301.21; 8/648; 570/128
[58] Field of Search ............. 570/128; 252/301.21; 8/648

[56] References Cited

U.S. PATENT DOCUMENTS

| 3,825,534 | 7/1974 | Weber et al. | 570/128 |
| 4,008,224 | 2/1977 | Siegrist et al. | |
| 4,097,515 | 6/1978 | Siegrist et al. | |
| 4,274,062 | 6/1981 | Brinkmann et al. | 372/53 |
| 4,330,427 | 5/1982 | Martini et al. | 252/301.21 |
| 4,380,514 | 4/1983 | Seybold | 252/301.21 |
| 4,464,284 | 8/1984 | Seybold | |

FOREIGN PATENT DOCUMENTS 1360279 7/1984 United Kingdom .

OTHER PUBLICATIONS

Rubel Optical Brighteners; Noyes Data Corp., Park Ridge, N.J., 1974, pp. 62-63.

Primary Examiner—Arthur P. Demers
Attorney, Agent, or Firm—Sprung Horn Kramer & Woods

[57] ABSTRACT

Distyryl compounds of the formula (I)

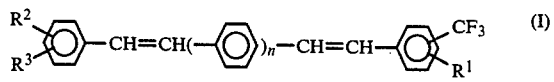

wherein
$R^1$ denotes hydrogen, halogen, alkyl and the like,
$R^2$ denotes hydrogen, halogen, aryl, alkyl, aralkyl and the like,
$R^3$ denotes hydrogen, halogen, alkyl or $CF_3$ and
n denotes 1 or 2, are useful fluorescent brighteners which are distinguished by their low degree of self-coloring. They are particularly useful for application to polyester fibre materials by thermosoling.

7 Claims, No Drawings

DISTYRYL COMPOUNDS

The invention provides compounds of the general formula

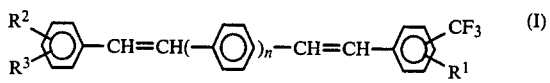

wherein $R^1$ denotes hydrogen, halogen, alkyl, alkoxy, aminocarbonyl, cyano, sulpho, acyl, acylamino, hydroxyl, aryloxy, aralkoxy, alkoxycarbonyl or acyloxy, $R^2$ denotes hydrogen, halogen, aryl, alkyl, aralkyl, hydroxyl, alkoxy, aralkoxy, aryloxy, sulpho, carboxyl, alkoxycarbonyl, aryloxycarbonyl, aralkoxycarbonyl, aminocarbonyl or cyano, $R^3$ denotes hydrogen, halogen, alkyl or $CF_3$ and n denotes 1 or 2 and wherein the cyclic or acyclic radicals may contain non-chromophoric substituents.

The new compounds of the formula I and their mixtures are useful fluorescent brighteners, which, by virtue of their low degree of self-colouring, are highly suitable for brightening synthetic fibre materials, in particular polyester fibres. Particular points in their favour, when used in this way, are that the fixing temperature is much reduced and especially that there is a complete absence of discoloured selvedges on stentered fabric webs during thermosoling.

In this respect they are far superior to conventional distyryl brighteners. They are even clearly superior to the quite recently developed biscyanostyrylbenzenes described in European Patent Specification Nos. A 23,027 and 64,303.

The new distyryl compounds even demonstrate their superiority as regards whiteness and the yield on application by the exhaust method at bath temperatures of 100° C., preferably 100° to 130° C. (high-temperature method).

The radicals named in the formula I have the following preferred meanings:

Non-chromophoric substituents are those customary in brightener chemistry, for example, halogen, alkyl, aryl, aralkyl, alkoxy, alkoxycarbonyl, aminocarbonyl, cyano, sulpho, aminosulphonyl, acyl, acylamino, hydroxyl, aryloxy, aralkyloxy, carboxyl or acyloxy.

Alkyl is in particular $C_1$-$C_4$-alkyl which may be monosubstituted by hydroxyl, $C_1$-$C_4$-alkoxy, cyano, carboxyl, $C_1$-$C_4$-alkoxycarbonyl, aminocarbonyl, chlorine or bromine or is trifluoromethyl.

Aryl is in particular phenyl which is optionally substituted by $C_1$-$C_4$-alkyl, trifluoromethyl, chlorine, bromine, carboxyl, cyano, $C_1$-$C_4$-alkoxycarbonyl or $C_1$-$C_4$-alkoxy.

Aralkyl is in particular phenyl-$C_1$-$C_4$-alkyl, which may be additionally substituted in the phenyl nucleus by chlorine, methyl or methoxy.

Alkoxy is in particular $C_1$-$C_4$-alkoxy.

Acyl is in particular $C_1$-$C_4$-alkylcarbonyl, $C_1$-$C_4$-alkoxycarbonyl, $C_1$-$C_4$-alkylsulphonyl, $C_1$-$C_4$-alkoxysulphonyl, optionally methyl-, methoxy- or chlorine-substituted benzoyl, optionally methyl-, methoxy- or chlorine-substituted benzenesulphonyl, optionally methyl-, methoxy- or chlorine-substituted phenyl-$C_1$-$C_4$-alkoxycarbonyl, or optionally methyl-, methoxy- or chlorine-substituted phenoxycarbonyl.

Particularly useful compounds have the formula

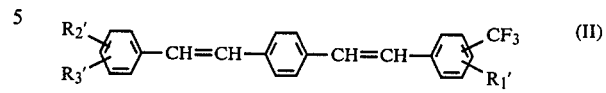

wherein $R_1'$ denotes hydrogen or chlorine, $R_2'$ denotes hydrogen, chlorine, phenyl, $C_1$-$C_4$-alkoxycarbonyl, $C_1$-$C_4$-alkylsulphonyl, optionally chlorine-, $C_1$-$C_4$-alkyl- or $C_1$-$C_4$-alkoxy-substituted phenylsulphonyl or cyano and $R_3'$ denotes hydrogen, chlorine or $CF_3$.

Of these, the asymmetrical types are very particularly preferred.

Of particular technical interest are mixtures of the symmetrical compounds, the asymmetrical compounds and the corresponding non-$CF_3$-containing symmetrical compounds of the formula I and in particular of the formula II wherein $R_1'$ denotes hydrogen or chlorine, $R_2'$ denotes $C_1$-$C_4$-alkoxycarbonyl or cyano and $R_3'$ denotes hydrogen or chlorine.

Preferred mixtures have the following composition: 0 to 35% by weight of the symmetrical compound of the formula

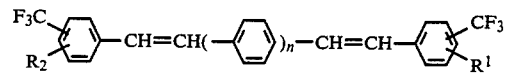

($R_1 = R_2$)

30 to 95% by weight of the asymmetrical compound of the formula

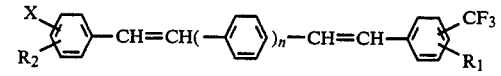

0 to 35% by weight of the compound of the formula

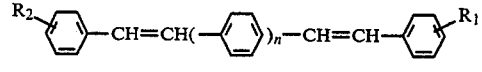

($R_1 = R_2$)

and corresponding mixtures of the formula II.

The distyryl compounds of the formula (I) can be prepared by methods known per se, namely by reacting the compound of the formula

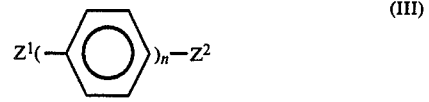

in the desired ratio with a compound each of the formulae

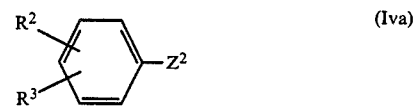

and

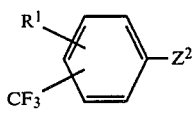

where one of the symbols $Z_1$ and $Z_2$ represents a formyl group and the other a grouping of the formula

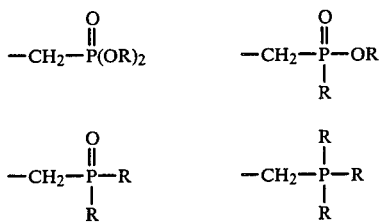

wherein R denotes a $C_1$–$C_4$-alkyl, a $C_5$–$C_6$-cycloalkyl or an optionally further substituted aryl radical, preferably a phenyl radical.

In this way symmetrical and asymmetrical compounds and mixtures of symmetrical and asymmetrical compounds can be prepared.

The phosphorus compounds of the formula (Iva), (Ivb) and (III), which are required as starting materials for the above reaction, can be obtained by reacting halogenomethyl compounds, preferably chloromethyl or bromomethyl compounds of the formulae

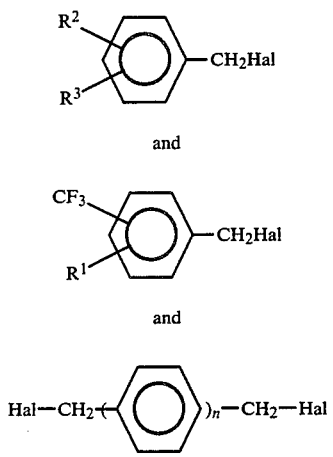

with phosphorus compounds $P(OR)_3$, $R$—$P(OR)_2$, $RO$—$P(R)_2$ or $P(R)_3$, where R is as defined above. Preferably, R bonded to oxygen denotes $C_1$–$C_4$-alkyl while bonded to phosphorus it denotes phenyl.

To prepare the end products, the appropriate components are condensed in organic solvents in the presence of basic condensing agents.

The chosen solvents are advantageously inert solvents, for example hydrocarbons such as toluene or xylene or alcohols such as methanol, ethanol, isopropanol, butanol, glycol, glycol ethers, such as 2-methoxyethanol, hexanol, cyclohexanol, or cyclooctanol, or ethers such as diisopropyl ether, dioxane or tetrahydrofuran, or formamides, N-methylpyrrolidone, dimethyl sulphoxide and phosphoramides. Dimethylformamide, dimethylacetamide and tris-dialkylamides of phosphoric acid where alkyl is in particular $C_1$–$C_4$-alkyl are preferred.

Suitable for use as condensing agents are strongly basic compounds, such as alkali metal and alkaline earth metal hydroxides, alkali metal and alkaline earth metal amides and alkali metal and alkaline earth metal alcoholates, for example potassium hydroxide, sodium hydroxide, potassium tert.-butylate, sodium amide or sodium methylate, the alkali metal compounds of dimethyl sulphoxide, alkali metal hydrides and, so far as they exist, alkali metal dispersions.

The preferred temperature range for the reaction is from 0° to 120° C.

The compounds (I) according to the invention are likewise obtained when the corresponding aldehyde-anils are reacted in the presence of basic condensing agents with the corresponding methyl compounds in a dipolar aprotic solvent, such as dimethylformamide.

In solution or in a finely divided state the compounds of the formula (I) display a very strong blue fluorescence. Alone or mixed they are suitable for brightening a very wide range of synthetic, cellulosic or natural organic materials.

Particularly preferred fields of application for the compounds and mixtures (above formula I) according to the invention are the following: fluorescent brightening of polyester, not only polyester fibres and fabrics—by the exhaust or pad-bake method—but also polyester spinning dopes. Blend fabrics of polyester and cotton or wool are likewise very advantageously brightened by means of the compounds according to the invention. Further substrates which can be brightened are nylon fibre fabrics, cellulose acetate fabrics as well as polystyrene and polyvinyl chloride materials. However, the particularly preferred use is for the fluorescent brightening of polyester fibres by the exhaust or pad-bake method or of polyester spinning dopes.

In these applications, the new brighteners are distinguished by high tinctorial strength, good build-up and a low tendency to shift towards green—even if the active substance is used in high concentrations.

The level of the compounds of the general formula I which are to be used in accordance with the invention, expressed relative to the material to be brightened, can vary within wide limits, according to the field of application and the desired effect. It can be easily determined by experiments and is generally between about 0.01 and about 2%.

The following Examples illustrate in more detail the preparation of the compounds and mixtures according to the invention and their use.

EXAMPLE 1

19.5 g (0.1 mole) of 4-trifluoromethylbenzyl chloride and 23.7 g (0.14 mole) of triethyl phosphite are mixed by stirring at the reflux temperature for 3 hours. Excess triethyl phosphite is then distilled off in vacuo, and 100 ml of anhydrous dimethylformamide are added to the residue. To this solution are added 21 g (0.09 mole) of 4-formyl-4'-cyanostilbene, followed by the dropwise addition at 50° C. in the course of 30 minutes of 18 g (0.1 mole) of 30% strength sodium methylate solution. The reaction mixture is stirred at 50° C. for 4 hours, and 5 g of acetic acid and 50 ml of methanol are added. The mixture is cooled down to room temperature, and the pale yellow crystalline precipitate is filtered off with suction, washed with a little methanol, and dried at 50° C. in vacuo. This gives 24.8 g (73.4% of theory) of pale yellow, almost colourless crystals which have a melting point of 220° to 224° C. and the formula $$F_3C-\text{C}_6H_4-CH=CH-\text{C}_6H_4-CH=CH-\text{C}_6H_4-CN \quad (1)$$

and which can be recrystallised from toluene (melting point 225° to 227° C.) UV absorption (in DMF) $\lambda_{max}=367$ nm $\epsilon_{max}=65,900$ Applied to polyester materials by thermosoling the substance produces an excellent reddish white and, in particular at low temperatures, has very good fixing properties.

EXAMPLE 2

In the same way as described in Example 1, 3-trifluoromethylbenzyl chloride is turned into 22.3 g (66% of theory) of almost colourless crystals of the compound of the formula $$\text{(3-CF}_3\text{-C}_6H_4\text{)}-CH=CH-\text{C}_6H_4-CH=CH-\text{C}_6H_4-CN \quad (2)$$

which can be reprecipitated from toluene.
Melting point: 132° to 134° C.
UV absorption (in DMF) $\lambda_{max}=365$ nm $\epsilon_{max}=62,900$ reddish fluorescence in DMF.

EXAMPLE 3

1.8 g of 30% strength sodium methylate solution are added dropwise at 30° C. in the course of 10 minutes to a mixture of 3.3 g (0.01 mole) of diethyl 2-chloro-4-trifluoromethylbenzylphosphonate and 2.34 g (0.01 mole) of 4-formyl-4'-cyanostilbene in 25 ml of dimethylformamide. The reaction mixture is stirred for 1 hour, and is cooled down to room temperature, when first a little acetic acid and then 10 ml of methanol are added, and the pale yellow mass of crystals is filtered off. In this way are obtained 2.8 g (68.3% of theory) of crude product of the formula $$NC-\text{C}_6H_4-CH=CH-\text{C}_6H_4-CH=CH-\text{C}_6H_3(Cl)-CF_3 \quad (3)$$

which can be purified by recrystallisation from isopropanol. Melting point: 178° to 180° C.
UV absorption (CHCl₃) $\lambda_{max}=366$ nm $\epsilon_{max}=59,200$
Fluorescence (in CHCl₃): brilliant bluish violet.

EXAMPLE 4

The following useful compounds of the formula $$A-\text{C}_6H_4-CH=CH-\text{C}_6H_4-CH=CH-\text{C}_6H_4-B \quad (4)$$

are prepared analogously to the method described in Examples 1 to 3 (see table).

TABLE I

| No. | A | B | UV absorption/ fluorescence (in DMF) $\lambda_{max}$ | $\epsilon_{max}$ | |
|---|---|---|---|---|---|
| 5 | 4-CN | 2-CF₃ | 364 nm | (62,000) | neutral blue |
| 6 | 4-CN | 3-CF₃ 4-Cl | 368 nm | (63,500) | slightly greenish blue |
| 7 | 4-CN | 3-CF₃ 2-Cl | 364 nm | (60,000) | bluish violet |
| 8 | 2-CN | 4-CF₃ | 360 nm | (50,250) | reddish blue |
| 9 | 2-CN | 3-CF₃ | 345 nm | (40,000) | strongly reddish blue |
| 10 | 2-CN | 2-CF₃ | 355 nm | (46,100) | blue |
| 11 | 2-CN | 4-CF₃ 2-Cl | 362 nm | (58,200) | intense blue |
| 12 | 2-CN | 3-CF₃ 2-Cl | 360 nm | (44,250) | reddish blue |
| 13 | 4-COOC₂H₅ | 4-CF₃ | 363 nm | (60,270) | slightly reddish blue |
| 14 | 4-CF₃ | 4-CF₃ | 360 nm | (61,700) | reddish blue |
| 15 | 4-CF₃ 2-Cl | 4-CF₃ 2-Cl | 352 nm | (50,600) | very reddish blue |
| 16 | 3-CF₃ 4-Cl | 3-CF₃ 4-Cl | 361 nm | (55,400) | blue |

EXAMPLE 5

2.7 g (0.02 mole) of 1,4-diformylbenzene, 5.3 g (0.021 mole) of diethyl 4-cyanobenzylphosphonate and 6.9 g (0.021 mole) of diethyl 2-chloro-4-trifluoromethylbenzylphosphonate are introduced into 20 ml of dimethylformamide. 9 g (0.05 mole) of 30% strength sodium methylate solution are added dropwise at room temperature with thorough stirring in the course of 30 minutes. The reaction mixture is stirred at 40° to 50° C. for 2 hours, 3 g of acetic acid are added, and the precipitate is filtered off. This gives 4.8 g of a greenish white crystalline powder of the composition:

72% $NC-\text{C}_6H_4-CH=CH-\text{C}_6H_4-CH=CH-\text{C}_6H_3(Cl)-CF_3$ (17)

8% $NC-\text{C}_6H_4-CH=CH-\text{C}_6H_4-CH=CH-\text{C}_6H_4-CN$

20% $F_3C-\text{C}_6H_3(Cl)-CH=CH-\text{C}_6H_4-CH=CH-\text{C}_6H_3(Cl)-CF_3$ which was determined by thin layer chromatography.
UV absorption (CHCl₃) $\lambda_{max}=362$ nm, $\epsilon_{max}=51,750$.

The mixture produces an excellent white on polyester materials when applied by high-temperature exhaust and thermosoling methods; a high whiteness yield without greening of the selvedges is obtained in particular at low thermosoling temperatures.

EXAMPLE 6

19.8 g (0.11 mole) of 30% strength sodium methylate solution are added dropwise at room temperature with thorough stirring in the course of 2 hours to a mixture of 12.8 g (0.05 mole) of diethyl 4-cyanobenzylphosphonate, 14.8 g (0.05 mole) of diethyl 2-trifluoromethylbenzylphosphonate and 6.4 g (0.048 mole) of 1,4-diformylbenzene in 50 ml of dimethylformamide. After 2 hours at 40° to 50° C. the reaction mixture is brought to pH 4–5 with a little acetic acid, and the pale yellow mass of crystals is filtered off, washed with methanol and dried. This gives 15.2 g of a mixture of the following composition:

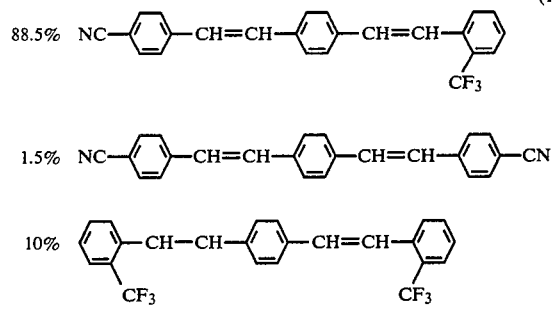

which was determined by thin layer chromatography. UV absorption (CHCl$_3$): $\lambda_{max}=359$ nm $\epsilon_{max}=59,000$.

The mixture produces a very good reddish white on polyester on application by the high-temperature exhaust and thermosoling methods.

EXAMPLE 7

In the same way as described in Example 5, 3.8 g (0.028 mole) of 1,4-diformylbenzene, 7.6 g (0.03 mole) of diethyl 4-cyanobenzylphosphonate and 10 g (0.03 mole) of diethyl 4-chloro-3-trifluoromethylbenzylphosphonate are turned into 12 g of a pale yellow crystalline powder of a mixture of the composition

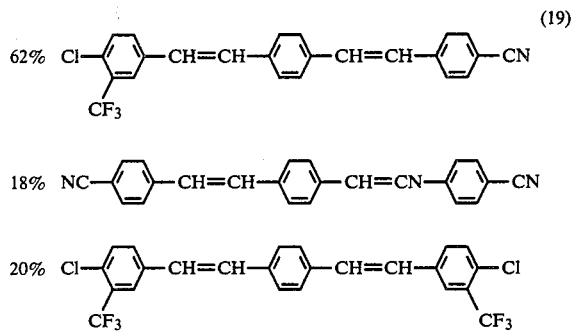

which was determined by thin layer chromatography. UV absorption (CHCl$_3$): $\lambda_{max}=362$ nm $\epsilon_{max}=54,200$.

EXAMPLE 8

A solution of 25 ml of dimethylformamide, 26.7 g (0.09 mole) of diethyl 4-trifluoromethylbenzylphosphonate and 17.1 g (0.095 mole) of 30% strength sodium methylate solution is added dropwise at 40° C. with thorough stirring in the course of 15 minutes to a solution of 9.6 g (0.07 mole) of 1,4-diformylbenzene in 25 ml of dimethylformamide. The reaction mixture is then stirred at 40° to 50° C. for 2 hours, and a solution of 25 ml of dimethylformamide, 12.7 g (0.05 mole) of diethyl 4-cyanobenzylphosphonate and 9.9 g (0.055 mole) of 30% strength sodium dimethylate solution is then added dropwise. The mixture is again stirred at 40° to 50° C. for 2 hours, 4 g of acetic acid are added, the solvent is removed under a water jet vacuum, and 50 ml of methanol are added to the residue. Filtering with suction and drying the filter residue gives 15.3 g of pale yellow crystalline powder of the following composition (determined by thin layer chromatography):

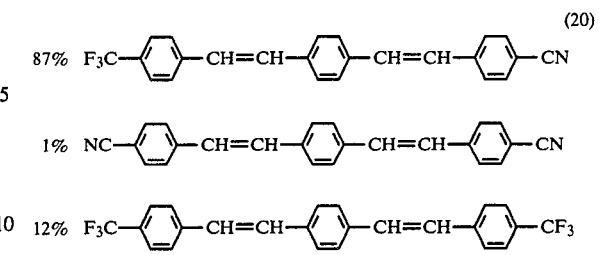

which is highly suitable for brightening polyester. UV absorption (in DMF): $\lambda_{max}=366$ nm $\epsilon_{max}=61,300$.

EXAMPLE 9

Example 8 is repeated and 10.7 g (0.08 mole) of 1,4-diformylbenzene are reacted with, in succession, 26.7 g (0.09 mole) of diethyl 3-trifluoromethylbenzylphosphonate and 15.2 g (0.06 mole) of diethyl 4-cyanobenzylphosphonate. This gives a brightener mixture of the following composition:

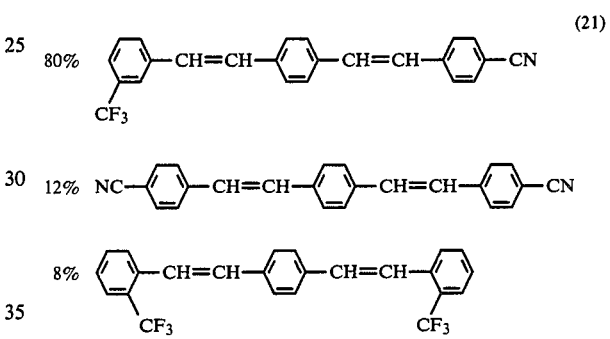

which was determined by thin layer chromatography. UV absorption (in DMF): $\lambda_{max}=367$ nm $\epsilon_{max}=60,500$.

We claim:

1. A distyryl compound of the formula

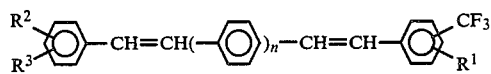

wherein $R^1$ is hydrogen, halogen, alkyl, alkoxy, aminocarbonyl, cyano, acyl, acylamino hydroxyl, aryloxy, aralkoxy, alkoxycarbonyl or acyloxy, $R^2$ is hydrogen, halogen, aryl, alkyl, aralkyl, hydroxyl, alkoxy, aralkoxy, aryloxy, carboxyl, alkoxycarbonyl, aryloxycarbonyl, aralkoxycarbonyl, aminocarbonyl or cyano, $R^3$ is hydrogen, halogen, alkyl or CF$_3$, and N is 1 or 2, and wherein said alkyl radicals are C$_1$-C$_4$-alkyl which may be monosubstituted by hydroxyl, C$_1$-C$_4$-alkoxy, cyano, carboxyl, C$_1$-C$_4$-alkoxycarbonyl, aminocarbonyl, chlorine or bromine or is trifluoromethyl; said aryl is phenyl which may be substituted by C$_1$-C$_4$-alkyl, trifluoromethyl, chlorine, bromine, carboxyl, cyano, C$_1$-C$_4$-alkoxycarbonyl, or C$_1$-C$_4$-alkoxy; said aralkyl is phenyl-C$_1$-C$_4$-alkyl, which may be substituted in the phenyl nucleus by chlorine, methyl or methoxy, said alkoxy is C$_1$-C$_4$-alkoxy and said acyl is C$_1$-C$_4$-alkyl-carbonyl, C$_1$-C$_4$-alkoxycarbonyl, C$_1$-C$_4$-alkylsulphonyl, C$_1$-C$_4$-alkoxysulphonyl, optionally methyl-, methoxyor chlorine-substituted benzoyl, benzenesulphonyl, phenyl-$C_1$-$C_4$-alkoxycarbonyl, or phenoxycarbonyl.

2. A distyryl compound according to claim 1 of the formula (II)

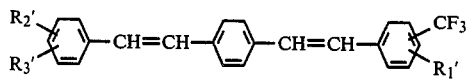

wherein $R_1'$ denotes hydrogen or chlorine, $R_2'$ denotes hydrogen, chlorine, phenyl, $C_1$-$C_4$-alkoxycarbonyl, $C_1$-$C_4$-alkylsulphonyl, optionally chlorine-, $C_1$-$C_4$-alkyl- or $C_1$-$C_4$-alkoxy-substituted phenylsulphonyl or cyano and $R_3'$ denotes hydrogen, chlorine or $CF_3$.

3. A distyryl compound according to claim 1 of the formula (II)
wherein $R_1'$ denotes hydrogen or chlorine, $R_2'$ denotes $C_1$-$C_4$-alkoxycarbonyl or cyano and $R_3'$ denotes hydrogen or chlorine.

4. A mixture of compounds according to claim 1 which consists of symmetrical compounds, asymmetrical compounds and the corresponding non-$CF_3$-containing symmetrical compounds of the indicated formulae.

5. A mixture according to claim 4, consisting of 0 to 35% by weight of a symmetrical compound, 30 to 95% by weight of an asymmetrical compound and 0 to 35% by weight of the corresponding non-$CF_3$-containing symmetrical compound.

6. In the fluorescent brightening of an article by application thereto of an optical brightener, the improvement wherein such optical brightener comprises a distyryl compound according to claim 1.

7. In the fluorescent brightening of an article comprising polyester fiber by applying an optical brightener to the article, and baking the article, the improvement which comprises employing as such optical brightener a distyryl compound according to claim 1.

* * * * *